United States Patent [19]

Yamori et al.

[11] Patent Number: 5,034,330
[45] Date of Patent: Jul. 23, 1991

[54] PREPARATION OF A SELECTIVELY PERMEABLE MEMBRANE FOR AN ENZYME ELECTRODE

[75] Inventors: Tsunefumi Yamori, Kobe; Eiji Yuasa, Amagasaki; Ryuzo Hayashi, Higashiosaka, all of Japan

[73] Assignee: Kanzaki Paper Mfg. Co., Ltd., Tokyo, Japan

[21] Appl. No.: 301,032

[22] Filed: Jan. 24, 1989

[30] Foreign Application Priority Data

Jan. 25, 1988 [JP] Japan ................................ 63-15130

[51] Int. Cl.$^5$ ........................ C12M 1/40; C12N 11/08; C12N 11/04; G01N 27/26
[52] U.S. Cl. .................................... 435/288; 204/403; 435/180; 435/182; 435/817
[58] Field of Search ............... 435/180, 182, 288, 817; 204/403

[56] References Cited

U.S. PATENT DOCUMENTS

| | | | |
|---|---|---|---|
| 3,860,490 | 1/1975 | Guttag | 435/182 |
| 4,356,074 | 10/1982 | Johnson | 204/195 |
| 4,795,707 | 1/1989 | Niiyama et al. | 435/817 X |

FOREIGN PATENT DOCUMENTS

| | | | |
|---|---|---|---|
| 228259 | 7/1987 | European Pat. Off. | |
| 2903216 | 8/1979 | Fed. Rep. of Germany | 435/817 |

OTHER PUBLICATIONS

Y. Hanazato et al.: "Application of Water-Soluble Photocrosslinkable Polymer to Enzyme Membrane for Fet-Biosensor," Proc. of 2nd International Meeting on Chemical Sensors, Bordeaux, Jul. 7–11, 1986, pp. 576–579.

I. Takatsu et al., "Solid State Biosensors Using Thin-Film Electrodes", Sensors and Activators, vol. 11, 1987, pp. 309–317.

Primary Examiner—David M. Naff
Attorney, Agent, or Firm—Wenderoth, Lind & Ponack

[57] ABSTRACT

A selectively permeable membrane for an enzyme electrode is prepared by forming a mixture of an emulsion of resin containing at least one prepolymer or monomer having ethylenic unsaturation, and a water-soluble polymer material, and subjecting the mixture to irradiation with ionizing or ultraviolet irradiation. The membrane is permeable to substances produced by an enzyme reaction while preventing the permeation of higher molecular weight materials. An immobilized enzyme membrane is formed on an outer surface of the permeable membrane, and the resultant membrane is mounted on an electrically conductive base to form an enzyme electrode. In another embodiment, the selectively permeable membrane is formed on the electrically conductive base, and then the immobilized enzyme membrane is formed. The selectively permeable membrane is situated between the immobilized enzyme membrane, which is in contact with a sample solution, and the electrically conductive base.

19 Claims, 2 Drawing Sheets

PREPARATION OF A SELECTIVELY PERMEABLE MEMBRANE FOR AN ENZYME ELECTRODE

BACKGROUND OF THE INVENTION

1. Field of the Invention

This invention relates to immobilized enzyme electrodes (hereinafter abbreviated as "enzyme electrode"), and in particular to enzyme electrodes which permit accurate measurements without any influence of electrochemically interfering substances.

2. Description of the Prior Art

Enzyme reactions are widely used in the quantitative analysis of objective substances contained in biosubstances, foodstuffs, etc. because of advantages such as high reaction rate and substrate specificity.

In particular, methods of measuring the concentration of objective substances by use of enzyme electrodes have developed the possibility of repeated use of a minute quantity of enzyme and are spreading their application to the range such as medical service, foodstuff, and chemicals analysis. The amperometric method which measures the current accompanying the electrode reaction of the product by enzyme reaction while applying a constant voltage to the enzyme electrode is widely studied because of the generally simple electrode construction and possible high-sensitivity measurements. Especially, an electrode using an oxidase forming hydrogen peroxide (called $H_2O_2$ forming oxidase) reaction system is relatively excellent in response speed and sensitivity. This method, however, has a drawback that the concentration of the objective substance cannot be accurately measured if an oxidizable material is present in the object to be examined.

For example, glucose determination using glucose oxidase (GOD) is described here.

$$\text{Glucose} + \text{Oxygen} \xrightarrow{\text{GOD}} \text{D-glucono-}\delta\text{-lactone} + H_2O_2 \quad \text{(i)}$$

The hydrogen peroxide produced according to equation (i) at an enzyme electrode with immobilized GOD causes electrode reaction by a voltage of about +0.6 V to a saturated calomel electrode as shown by equation (ii)

$$H_2O_2 \rightarrow O_2 + 2H^+ + 2e^- \ldots \quad \text{(ii)}$$

The current produced here, which is proportional to the glucose concentration, makes the determination of the glucose concentration possible.

The enzyme reaction represented by equation (i) has a high substrate specificity to glucose, the objective substance. However, the electrode reaction represented by (ii) is not specific to hydrogen peroxide and oxidizes various reducing substances, that is, electrochemical interfering substances on the electrode. Thus, the current produced by the oxidation of the interfering substances is added to the measured current, causing an error. It is known that foodstuffs and biological liquid used for measurement contain electrochemical interfering substances such as ascorbic acid, uric acid, reduced glutathione, and tyrosine. Thus, the development of a method for solving the above measuring error has been strongly requested.

A method has been known which answers such a request, in which the current is measured under condition that only hydrogen peroxide is permeated without interfering substances having larger molecular weight than the hydrogen peroxide permeated, by provision of selectively permeable membrane consisting of acetylcellulose, between the immobilized enzyme membrane and the electrically conductive substrate such as platinum in the enzyme electrode for measuring hydrogen peroxide which is produced by the oxidase reaction represented by equation (i).

However, a conventional selectively permeable membrane such as acetylcellulose membrane requires complex adjustment of the degree of acetylation, dissolving method, membrane forming method, and mixing quantity of trifunctional amine, so it is difficult to prepare a selectively permeable membrane of the same quality with good reproducibility.

SUMMARY OF THE INVENTION

It is an object of the invention to provide an enzyme electrode which permits accurate measurement without any influence of interfering substances by providing a selectively permeable membrane having excellent selective permeability, with good reproducibility.

To attain the above object, the present invention provides an enzyme electrode comprising:

(a) a selectively permeable membrane composed of a mixed composition comprising an emulsion of resin curable by irradiation of ionizing radiation or ultraviolet ray and a water-soluble polymer material, obtained by curing the mixed composition with irradiation of ionizing radiation or ultraviolet ray, and for permeating the substances produced by enzyme reaction selectively;

(b) an immobilized enzyme membrane formed on one surface of the selectively permeable membrane; and (c) an electrically conductive base mounted the selectively permeable membrane with the immobilized enzyme membrane formed thereon, so that the selectively permeable membrane faces the electrically conductive base having the surface where the immobilized enzyme membrane is not formed.

According to the invention, the selectively permeable membrane may face the electrically conductive base directly or through electrolytic solution.

As the electrically conductive base according to the invention, platinum, gold, and carbon are used.

The emulsion of resin curable by irradiation of ionizing radiation or ultraviolet ray for the formation of the selectively permeable membrane according to the invention contains at least one type of prepolymer or monomer having ethylenic unsaturated double bond.

Examples of useful electron beam-curable or ultraviolet ray curable prepolymers include:

(a) Poly(meth)acrylates of aliphatic, alicyclic, or araliphatic polyhydric (having from 2 to 6 alcoholic hydroxy groups) alcohols or polyalkylene glycols, such as esterified compounds of polyhydric alcohols (e.g., ethylene glycol and propylene glycol) or polyalkylene glycols (e.g., polyethylene glycol) and (meth)acrylic acid;

(b) Poly(meth)acrylates of polyhydric alcohols resulting from addition of alkylene oxides to aliphatic, alicyclic or araliphatic polyhydric (having from 2 to 6 alcoholic hydroxy groups) alcohols, such as esterified compounds of polyhydric alcohols resulting from addition of alkylene oxides (e.g., ethylene oxide) to polyhydric alcohols (e.g., pentaerythritol) and (meth)acrylic acid;

(c) Poly(meth)acryloyloxyalkyl phosphates resulting from reaction of hydroxy group-containing (meth)acrylates and phosphorus pentoxide, e.g., poly(meth)acryloyloxyethyl phosphate;

(d) Polyester poly(meth)acrylates resulting from esterification of (meth)acrylic acid, polyhydric alcohols, and polycarboxylic acids, e.g., di(meth)acrylate of polyester diol between maleic acid and ethylene glycol, di(meth)acrylate or polyester diol between phthalic acid and diethylene glycol, and poly(meth)acrylate of polyester diol between adipic acid and triethylene glycol;

(e) Epoxy poly(meth)acrylates which are a reaction product of (meth)acrylic acid and epoxy resin resulting from reaction of polyhydric phenols and epichlorohydrin, e.g., a reaction product of bisphenol A-diglycidyl ether-based epoxy resin and (meth)acrylic acid;

(f) Polyurethane poly(meth)acrylates such as reaction products of hydroxy group-containing (meth)acrylates (e.g., 2-hydroxyethyl (meth)acrylate) and diisocyanate;

(g) Polyamide poly(meth)acrylates such as reaction products of polyamide-based polycarboxylic acids (e.g., that result from reaction of ethylenediamine and phthalic acid) and hydroxy group-containing (meth)acrylates (e.g., 2-hydroxyethyl (meth)acrylate);

(h) Polysiloxane poly(meth)acrylates such as reaction products of polysiloxane bond unit-containing polyhydric alcohols and (meth)acrylic acid or hydroxy group-containing (meth)acrylates;

(i) Low molecular weight vinyl or diene polymers containing (meth)acryloyloxy group in the side chain and/or terminal thereof, such as reaction products of copolymers of (meth)acrylic acid and other vinyl monomer and glycidyl (meth)acrylate; and (j) Modified products of the oligoester (meth)acrylates of (a) to (i) above, such as modified products obtained by modifying a part of the hydroxy or carboxyl groups remaining in the oligoester with an acid chloride, an acid anhydride, or an isocyanate.

Examples of useful electron beam-curable or ultraviolet ray curable monomers include:

I. Monofunctional Unsaturated Monomers (1) Carboxyl group-containing monomers exemplified by ethylenically unsaturated mono- or poly-carboxylic acids (e.g., maleic acid, fumaric acid, and itaconic acid), and carboxylic acid salt group-containing monomers such as alkali metal salts, ammonium salts, and amine salts of the foregoing monomers;

(2) Amide group-containing monomers exemplified by ethylenically unsaturated (meth)acrylamides or alkylsubstituted (meth)acrylamides (e.g., N,N-dimethyl(meth) acrylamide), and vinyl lactams (e.g., N-vinylpyrrolidone);

(3) Sulfonic acid group-containing monomers exemplified by aliphatic or aromatic vinylsulfonic acids, and sulfonic acid salt group-containing monomers such as the alkali metal, ammonium and amine salts of the foregoing vinylsulfonic acids, e.g., 2-acrylamido-2-methylpropanesulfonic acid;

(4) Hydroxyl group-containing monomers exemplified by ethylenically unsaturated esters, such as tripropylene glycol mono(meth)acrylate;

(5) Amino group-containing monomers such as dimethylaminoethyl (meth)acrylate and 2-vinylpyridine;

(6) Quaternary ammonium salts group-containing monomers such as N,N,N-trimethyl-N-(meth)acryloyloxyethylammonium chloride;

(7) Alkyl esters of ethylenically unsaturated carboxylic acids, such as methyl (meth)acrylate and ethyl (meth)acrylate;

(8) Nitrile group-containing monomers such as (meth)acrylonitrile:

(9) Styrene;

(10) Ethylenically unsaturated alcohol esters such as vinyl acetate and (meth)allyl acetate; and

(11) Mono(meth)acrylates of alkylene oxide adducts of compounds containing active hydrogen (e.g., monohydric alcohols, phenols, carboxylic acids, amines, and amides).

II. Difunctional Unsaturated Monomers (1) Ester group-containing difunctional monomers exemplified by diesters of polyols and ethylenically unsaturated carboxylic acids, such as trimethylolpropane di(meth)acrylate, and diesters of polybasic acids and unsaturated alcohols, such as diallyl phthalate;

(2) Difunctional diesters of (meth)acrylic acid and alkylene oxide adducts of compounds containing active hydrogen (e.g., polyhydric alcohols, phenols, carboxylic acids, amines, and amides) such as pentanediol propylene oxide adduct;

(3) Bisacrylamides such as N,N-methylenebisacrylamide; and (4) Difunctional compounds such as divinylbenzene, divinylethylene glycol, divinylsulfone, divinyl ether, and divinyl ketone.

III. Polyfunctional Unsaturated Monomers (1) Ester group-containing polyfunctional monomers exemplified by polyesters of polyols and ethylenically unsaturated carboxylic acids, such as trimethylolpropane (meth)acrylate and dipentaerythritol hexa(meth)acrylate, and polyesters of polycarboxylic acids and unsaturated alcohols, such as triallyl trimellitate;

(2) Polyfunctional monomers exemplified by polyesters of alkylene oxide adducts of compounds containing active hydrogen (e.g., polyhydric alcohols, polyhydric phenols, polycarboxylic acids, polyamines, and polyamides) and (meth)acrylic acid; and (3) Polyfunctional unsaturated momomers such as trivinylbenzene.

Water-dispersible prepolymers or monomers are generally stirred with water in the presence of a surfactant (surface active agent) to form an oil-in-water type emulsion.

Examples of surfactants which may be used include anionic surfactants such as fatty acid salts, higher alcohol sulfuric acid ester salts, alkylbenzenesulfonic acid salts, alkylnaphthalenesulfonic acid salts, a naphthalenesulfonic acid/formalin condensate, dialkylsulfosuccinic acid salts, alkyl phosphate salts, and polyoxyethylene sulfate salts; nonionic surfactants such as polyoxyethylene alkyl ethers, [polyoxyethylene alkylphenol ethers, sorbitan fatty acid esters, polyoxyethylene] sorbitan fatty acid esters, and polyoxyethylene acyl esters; cationic surfactants such as alkylamine salts, quaternary ammonium salts, and polyoxyethylenealkylamines; and water-soluble polymers such as polyvinyl alcohol. These surfactants may be used singly or in combination with each other. Of these compounds, nonionic surfactants having an HLB of at least 10 are preferable to obtain emulsions having greatly increased stability.

The amount of the surfactant used is usually from 0.01 to 20% by weight, preferably from 0.05 to 10% by weight, based on the weight of the monomer or prepolymer.

The water soluble polymer material includes;
cellulose derivatives such as methyl cellulose, hydroxyethyl cellulose, ethylhydroxyethyl cellulose, carboxymethyl cellulose, and viscose;
starch or its derivatives such as soluble starch, oxidized starch, and dextrin;
those containing polysaccharides such as gum arabic, tragacanth and alginic acid;
proteins such as glue, gelatine, casein, albumin, soybean-protein, and enzyme;
sodium polyacrylate;
ethylene oxide polymers such as polystyrene glycol and polyethylene oxide;
polyvinyl ethers such as polyvinylmethyl ether, polyvinylethyl ether, and polyvinylisobutyl ether;
completely saponified or partially saponified polyvinyl alcohol;
acetoacetylated polyvinyl alcohol with acetoacetyl group introduced by reaction of polyvinyl alcohol and diketene;
esterified products and ester derivatives of the products of polyvinyl alcohol with multivalent carboxylic acid such as fumaric acid, phthalic anhydride, trimellitic anhydride, and itaconic anhydride;
carboxymodified polyvinyl alcohol obtained as the saponification product of the copolymer of vinyl acetate with an ethylenic unsaturated carboxylic acid such as maleic acid, fumaric acid, itaconic acid, crotonic acid, acrylic acid, and methacrylic acid;
sulfonic acid modified polyvinyl alcohol obtained as a saponification product of copolymer of vinyl acetate with an olefin sulfonic acid such as ethylenesulfonic acid and allylsulfonic acid, or with its salt;
olefin modified polyvinyl alcohol;
nitrile modified polyvinyl alcohol; and
amide modified polyvinyl alcohol;
pyrrolidone modified polyvinyl alcohol.

According to the preferred embodiment of the invention, among these water soluble polymer materials, various modified polyvinyl alcohols, gelatine, and gum arabic are favorable from the viewpoint of the selective permeability, and particularly preferable are acetoacetylated polyvinyl alcohol and gelatine, The mixed composition of the emulsion of resin curable by ionizing radiation or ultraviolet ray (hereinafter abbreviated as specific emulsion of resin) and the water soluble polymer material may further contain styrene-butadiene copolymer emulsion, vinyl acetate-vinyl chloride-ethylene copolymer emulsion, metacrylate-butadiene copolymer emulsion, etc.

The mixing ratio of the above specific emulsion of resin and water-soluble polymer material is adjusted depending on the molecular weight of the interfering substance and the durability required of the electrode. Too small a quantity of water-soluble polymer material can fail to give sufficient selective permeability, and too large a quantity of water-soluble polymer material can fail to give sufficient physical strength. Therefore, 0.1 to 100 parts by weight, preferably 1 to 50 parts by weight of the water-soluble polymer material is mixed with 100 parts by weight of the specific emulsion of resin.

The selectively permeable membrane according to the invention is prepared by the following method: The solution containing the water-soluble polymer material is mixed with the specific emulsion of resin, and the mixed composition is molded so that a membrane thickness of 0.1–500 $\mu$m after drying is obtained or it is directly applied on the electrically conductive base, and cross-linked by the irradiation of ionizing radiation or ultraviolet ray.

When gelatine is used as the water-soluble polymer material, for example, an aqueous gelatine solution of about 10% concentration is prepared by heating in an autoclave or the like. The gelatine solution is mixed with a specific emulsion of resin by stirring at about 40° C. Then, the mixed composition is applied on a base film such as polyester and polypropyrene film so that after drying a thickness of 0.1–500 $\mu$m of the mixed composition membrane is obtained. The solvent is dissipated at about 40° C., and the membrane obtained is irradiated with electron beam and pealed off the base film to give a selectively permeable membrane.

It is also possible that the above mixed-composition solution is applied on a porous sheet such as cellulose, polyethylene, and polypropyrene so that a membrane thickness of 0.1–500 $\mu$m is obtained after drying, and the solvent is dissipated at about 40° C., the membrane is crosslinked with electron beam to give a selectively permeable membrane united with the porous sheet. This method has an advantage that the physical strength of the selectively permeable membrane can be reinforced, and even a thin selectively permeable membrane cannot be damaged during handling.

The thus obtained selectively permeable membrane has its selective permeability further increased by enough washing.

The ionizing radiation used in the invention includes election beam, alpha ray, beta ray, gamma ray, proton ray, X-ray, and neutron radiation. However, electron beam which can be produced with relatively simple equipment is preferably used.

The quantity of electron beam to be radiated is 0.1–10 Mrad, preferably 0.5–5 Mrad. Less than 0.1 Mrad cannot satisfactorily harden the resin component, and an excess electron irradiation over 10 Mrad can cause decomposition or a structure change of the watersoluble polymer material. The available electron beam irradiation method includes scanning system, curtain beam system, and broad beam system. The adequate acceleration voltage in irradiation is about 100–300 kV.

Similar crosslinking can be attained by ultraviolet ray irradiation, but it is necessary in this case to add a sensitizer in the mixed composition, which can deactivate the enzyme.

The thus obtained selectively permeable membrane is not only excellent in selective permeability but also has an advantage that it can be easily prepared. The mechanism of the selective permeability of the membrane is not always clear, but it is considered that the network of the specific emulsion involving the water-soluble polymer material, and the functional group of the water-soluble polymer material are playing an important role.

Then the enzyme is immobilized on the selectively permeable membrane thus formed. A hydrogen peroxide forming oxidase such as glucose oxidase, galactose oxidase, and alcohol oxidase is favorably used.

The enzyme is immobilized on a selectively permeable membrane by various known methods.

When an enzyme is immobilized by carrier bonding such as ionic bonding and covalent bonding, the solution containing the enzyme and the carrier, etc. shown below is applied on the selectively permeable membrane. The carrier used includes cellulose derivatives such as acetyl cellulose derivatives, nitrocellulose (such as collodion), various ion-exchange cellulose derivatives (such as DEAE-cellulose, TEAE-cellulose, EC-TEOLA-cellulose, and CM-cellulose); polysaccharides such as starch, dextran derivatives (such as Shephadex (trade name)), agarose, mannan, chitosan, carrageenan, alginic acid, xanthan gum, and ager; proteins such as collagen, gelatin, fibrion, keratin, albumin, and gluten; polymer gels such as polyacrylamide polyvinylpyrrolidone, and polyvinyl alcohol; synthetic organic polymer substances such as polyvinyl chloride, polymethyl methacrylate, polyacrylonitrile, polystyrene, polyaminostyrene, polyethylene, polypropylene, polyurethane, polycarbonate, polyamide (such as nylon and polyamino acids), fluoroplastics, silicone resin, photosetting resin, adsorption resin, and ion exchange resin. They are used intact or with a functional group reactive with the enzyme introduced, or with the functional group activated. To introduce a functional group, for forming covalent bond with the functional group, diazo method, peptide method, alkylation method, or with a method using a crosslinking reagent (such as glutaraldehyde and hexamethylene diisocyanate) are used. It is also possible to immobilize the enzyme by adsorption.

When using the crosslinking method, the enzyme can be immobilized with a reagent having two or more functional groups such as glutaraldehyde, isocyanate derivatives (such as hexamethylene diisocyanate and toluene diisocyanate), isothiocyanate derivatives (such as hexamethylene diisothiocyanate), N,N'-ethylenebismaleinimide, N,N'-(1,2-phenylene)-bismaleinimide, N,N'-(1,4phenylene)bismaleinimide, and N,N-polymethylenebisiodoacetoamide.

When the enzyme is immobilized by the inclusion method, it is taken into the gel lattice of such as polymer gel, cellulose derivative, polysaccharide, and protein. For example, the specific emulsion of resin and the enzyme are mixed with each other and thinly applied on the selectively permeable membrane, and is irradiated with ionizing radiation or ultraviolet ray to form an immobilized enzyme membrane. It is also possible to cover the enzyme with semipermeable membrane such as organic polymer substance and cellulose derivative into micro-capsule form and to apply it on the selectively permeable membrane.

It is also possible to combine two or more types of these methods for immobilizing the enzyme.

When preparing an immobilized enzyme membrane, the following method can be used. The enzyme is mixed into the specific emulsion of resin to be hardened by the irradiation of ionizing radiation or ultraviolet ray, and the mixed composition is applied on the formed selectively permeable membrane. The applied mixed composition is hardened by irradiation of ionizing radiation or ultraviolet ray into unitedly formed immobilized enzyme membrane and selectively permeable membrane. This method can produce a selectively permeable membrane and immobilized enzyme membrane of wide area at a time in good reproducibility and it effectively reduces the manufacturing cost of the enzyme electrode.

The mixing ratio of the enzyme and the specific resin emulsion is different depending upon the activity per unit weight of the enzyme and the detecting sensitivity of the objective enzyme electrode, but usually the enzyme is mixed in a range of 0.01-20% by weight on solid of the mixed composition comprising the resin emulsion and the enzyme. Too small a quantity of enzyme decreases the final sensitivity of the enzyme electrode, and too large a quantity decreases the membrane strength and causes problems of pealing of the immobilized enzyme membrane.

Depending upon the type and mixing quantity of the enzyme used, the immobilized enzyme may become extremely dense, leading to decreased diffusibility of the substrate of the enzyme reaction. This can decrease the enzyme reaction rate and deteriorate the measuring sensitivity. In such a case, an addition of water-soluble polymer material to the mixture of the emulsion of resin and the enzyme can increase the diffusion rate of the substrate and consequently increase the sensitivity of the enzyme electrode. For such purpose, the various water-soluble polymer materials exemplified above can be used. In particular, modified polyvinyl alcohol, gelatine, gum arabic, and alubumin are preferable because they can increase the diffusibility of substrate without adverse influence on the activity cf the enzyme. The watersoluble polymer material can give above described effect and satisfactory membrane strength when the enzyme and the water-soluble polymer material are added in a range of 0.1-50 wt % on dry basis of the mixed composition.

When manufacturing the immobilized enzyme membrane, the use of electron beam as ionizing radiation can immobilize the enzyme without decreasing the enzyme activity in comparison with other methods.

The thus manufactured selectively permeable membrane with immobilized enzyme is mounted on an electrically conductive base to give an enzyme electrode (working electrode). As the counter electrode, platinum, gold, carbon, etc. are used, and as the reference electrode, a saturated calomel electrode (SCE), Ag-/AgCl electrode, etc. are used. Each of 3-electrode method and 2 electrode method can be used as the electrode type.

The selectively permeable membrane with immobilized enzyme may be mounted in an end of a glass tube or plastic tube with a working electrode made of platinum, gold, or carbon, reference electrode, and counter electrode put in it and filled with the electrolyte solution. Or it is also possible to mount the selectively permeable membrane with immobilized enzyme on the surface of the electrically conductive base and provide the reference electrode or counter electrode on the outside. As the electrically-conductive tase, platinum, gold, carbon and so on, or an insulator on which electroconductive layer is formed by evaporation is used. And, enzyme electrode can be made as follows: a mixed composition solution containing the specific emulsion of resin and water-soluble polymer material can be directly applied on the surface of electrically-conductive base and hardened by ionizing radiation or ultraviolet ray and immobilize thereon the enzyme.

The enzyme electrode thus manufactured can be incorporated into an adequate cell and used for flow type measurement and for the batch type use as well.

Thus, the selectively permeable membrane with good reproducibility and excellent selective permeability prepared according to the invention provide the enzyme electrode permits accurate measurement free of the influence of interfering substances.

BRIEF DESCRIPTION OF THE DRAWINGS

These and other objects, features, and advantages will be more apparent from the drawings and the detailed description.

DESCRIPTION OF THE PREFERRED EMBODIMENTS

The following description is of best embodiments after mature consideration for implementing the invention. This is only for illustration of the general principle of the invention and not intended to limit the invention. The scope of the invention should be defined by the attached claims. In the description, "%" and "parts" represent "% by weight" and "parts by weight", respectively.

EXAMPLE 1

Preparation of Selectively Permeable Membrane

A mixed composition of 100 parts of electron beam curable emulsion of resin (trade name: Laromer PE 55W, made by BASF Co.) of 50% in concentration comprising polyester acrylate and 150 parts of aqueous 10% acetoacetylated polyvinyl alcohol as water-soluble polymer material was applied on polyethylene telephthalate film so that the coating quantity after drying becomes 20 g/m$^2$, and dried at 45° C. to give a membrane of mixed composition.

The mixed composition membrane was treated with an electron curtain type irradiator (CB: 150 type, made by ESI Co.) at an acceleration voltage of 165 kV, with an exposure of 2 Mrad to cure the resin component. The formed selectively permeable membrane was peeled off the polyethylene terephthalate film and washed with water for 15 hrs.

Immobilization of Enzyme

Filter paper (Trade name: Filter Paper No. 5A, made by Toyo Co.) was put on a clean glass plate and a selectively permeable membrane was spread thereon. An enzyme solution comprising 100 mM sodium phosphate buffer solution (pH 7.0) containing 10 mg/ml of glucose oxidase (derived from *Aspergillus niger*, made by Sigma Co., Trade name: Type II) and 10 mg/ml bovine serum albumin (made by Sigma Co., Fraction V) with an addition of glutaraldehyde to a concentration of 1.0% was developed on the selectively permeable membrane in a quantity of 100 μl/cm$^2$ and was left to stand for 1 hr at room temperature.

Measuring Method

Figure 1:
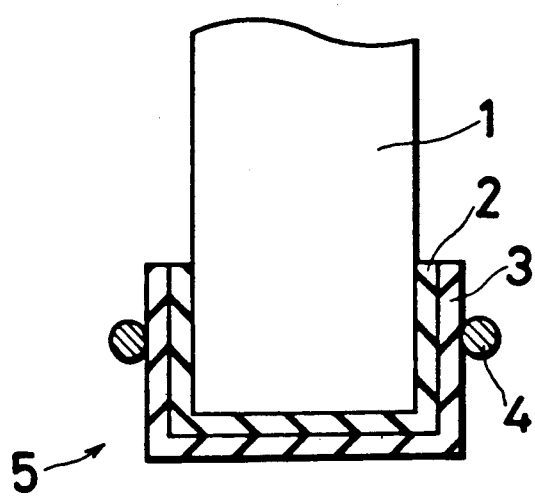
FIG. 1 is a sectional view of the enzyme electrode 5 used in Example 1 of the invention.

As shown in FIG. 1, the above selectively permeable membrane 2 was mounted on the end of a platinum wire 1 of 3 mm in diameter with an O-ring 4 with the immobilized enzyme membrane 3 outside to give a working electrode 5.

Figure 2:
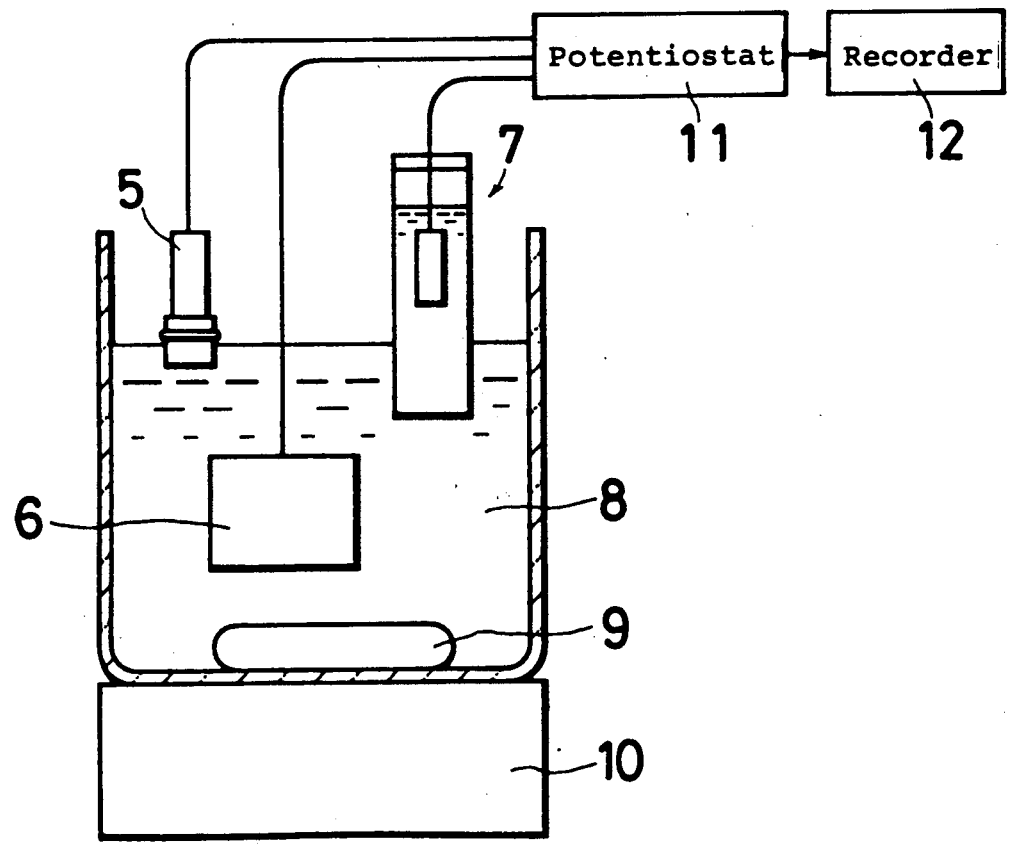
FIG. 2 is a view showing a measuring apparatus using the enzyme electrode 5.

The working electrode 5 was mounted on the measuring cell of a batch type measuring apparatus shown in FIG. 2 and immersed in 100 mM sodium phosphate buffer solution 8 of pH 7.0. Using a platinum plate of 1 cm square as the counter electrode 6 and SCE as the reference electrode 7, measurement was made with a potential applied to the working electrode 5 and a potential of +0.6 V to the reference electrode 7. To stir the sample, a magnetic stirrer 10 and a magnet 9 were used. The output current from the working electrode 5 was recorded with a recorder 12.

Glucose was added into the measuring cell in various concentrations, and the output current of the working electrode 5 was examined against each concentration of glucose (0.5–2.5 mM).

Then, the buffer solution was replaced with a new buffer solution and an aqueous solution containing 1 M of glucose and 0.1 M of ascorbic acid was added, and the output current at each glucose concentration (0.5–2.5 mM) was examined.

EXAMPLE 2

Measurement was made in the same manner as in Example 1, except that the enzyme electrode was prepared by use of acidic gelatine (trade name: NHG-16 made by Nitta Gelatine Co.) instead of the acetoacetylated polyvinyl alcohol.

EXAMPLE 3

Measurement was made in the same manner as in Example 1, except that the enzyme electrode was prepared by use of gum arabic (made by Kishida Chemical Co.) instead of the acetoacetylated polyvinyl alcohol.

COMPARATIVE EXAMPLE 1

An enzyme electrode was prepared and measurement was made in the same manner as in Example 1, except that acetoacetylated polyvinyl alcohol was not used in preparing the enzyme electrode.

COMPARATIVE EXAMPLE 2

Figure 3:
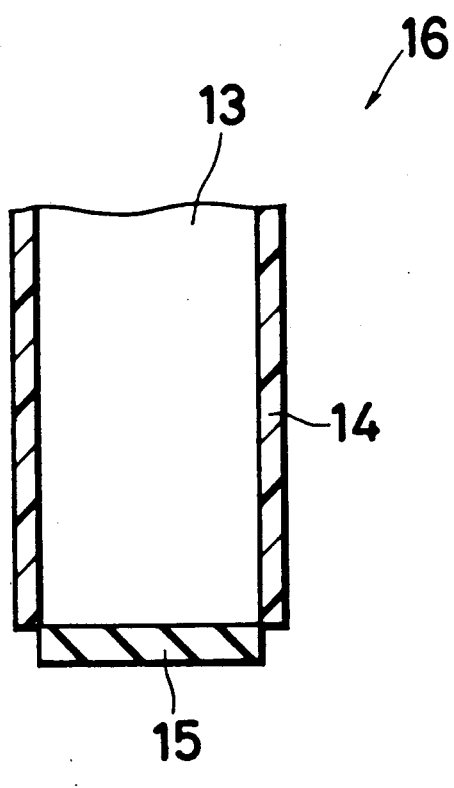
FIG. 3 is a sectional view of the enzyme electrode 16 used in Comparative Example 2.

As shown in FIG. 3, on a platinum wire 13 of 3 mm diameter was developed 100 μl/cm$^2$ of enzyme solution comprising 100 mM sodium phosphate buffer solution (pH 7.0) containing 10 mg/ml of glucose oxidase (derived from *Aspergillus niger*, made by Sigma Co., Trade name: Type II) and 10 mg/ml bovine serum albumin (made by Sigma Co., Fraction V) with an addition of gluta aldehyde to a concentration of 1.0%. After incubating at room temperature for 1 hr, a immobilized enzyme membrane 15 was formed. The side of the platinum wire 13 was covered by a heat-shrinkable Teflon cover 14. Thus, a working electrode 16 having no selectively permeable membrane was prepared and measurement was made in the same manner as in Example 1.

The results of these measurements are shown in Table 1.

TABLE 1

| | Output current in each Example and Comparative Example (μA) | | | | | |
| --- | --- | --- | --- | --- | --- | --- |
| | Glucose concentration | | | | | |
| | 0.5 mM | | 1.5 mM | | 2.5 mM | |
| | Presence of ascorbic acid | | | | | |
| Presence of | None | Present | None | Present | None | Present |
| Example 1 | 0.07 | 0.07 | 0.21 | 0.21 | 0.34 | 0.34 |
| Example 2 | 0.11 | 0.11 | 0.35 | 0.36 | 0.53 | 0.56 |
| Example 3 | 0.08 | 0.08 | 0.25 | 0.27 | 0.42 | 0.45 |
| Comparative Example 1 | 0.00 | 0.00 | 0.00 | 0.00 | 0.00 | 0.00 |
| Comparative Example 2 | 0.21 | 0.25 | 0.61 | 0.73 | 1.10 | 1.32 |

In Examples 1–3, the output current hardly changed depending upon the presence of ascorbic acid, and was not influenced by ascorbic acid, an interfering substance. It was found that the output current is proPortional to the concentration of glucose and can be used in measuring the glucose concentration. Particularly, in Example 1, where acetoacetylated polyvinyl alcohol was used, the influence of ascorbic acid was not observed at all.

In comparative example 1, where water-soluble polymer material was not used, the crosslinkage of the membrane became too dense to allow even hydrogen peroxide to permiate and, therefore, output current to glucose could not be obtained. Comparative example 2, where no selectively permeable membrane was used, had a large influence of ascorbic acid and was found not available for accurate determination of glucose concentration.

EXAMPLE 4

Preparation of Selectively Permeable Membrane

A mixed composition of 100 parts of electron beam curable emulsion of resin (trade name: Laromer PE55W, 50% concentration, made by BASF Co.) comprising polyesteracrylate and 100 parts of 5%-concentration acidic gelatine (trade name: NHG-16, made by Nitta Gelatine Co.) was applied on polyethylene terephthalate film so that the coating weight becomes 15 g/m$^2$ on dry basis and dried at 45° C. to give membrane of the mixed composition.

The mixed composition membrane was treated with an electroncurtain type irradiator (CB: 150 type, made by ESI Co.) at an acceleration voltage of 165 kV, with an exposure of 2 Mrad to harden the resin component.

Immobilization of Enzyme

On the prepared selectively permeable membrane a mixture of 1 ml of alcohol oxidase (derived from *Pichia pastolis*, made by Sigma Co.), 100 mg of bovine serum albumin, and 1 g of emulsion of resin (Laromer PE55W) was applied, and after drying at room temperature, irradiated with electron beam in the same conditions as when the selectively permeable membrane was prepared. After curing, it was peeled off the polyethylene terephthalate film and was washed with 100 mM sodium phosphate buffer solution (pH 7.5) for about 20 hrs.

Measuring Method

The sensitivity was examined in the same manner as in Example 1, except that the response to ethanol and ascorbic acid was examined by use of aqueous 1 M ethanol solution and aqueous 1 M ascorbic acid solution.

The results are shown in Table 2. From Table 2, it is understood that ascorbic acid shows a sensitivity only 5% or less in comparison with ethanol of the same concentration. And this means that the above method can give a membrane having excellent selective permeability, and that the alcohol oxidase is immobilized with high activity.

TABLE 2

| Output response value in Example 4 (nA) | | | | |
| --- | --- | --- | --- | --- |
| Ethanol/ascorbic acid concentration (mM) | 0.1 | 0.5 | 1.0 | 2.0 |
| Ethanol response value (nA) | 23 | 116 | 232 | 459 |

TABLE 2-continued

| Output response value in Example 4 (nA) | | | | |
| --- | --- | --- | --- | --- |
| Ascorbic acid response value (nA) | 2 | 2 | 4 | 7 |

As this invention may be embodied in several forms without departing from the spirit or essential characteristics thereof, the present embodiment is therefore illustrative and not restrictive, since the scope of the invention is defined by the appended claims rather than by the description preceding them. All modifications and changes that fall within meats and bounds of the claims are intended to be embraced by the claims.

What is claimed is:

1. An enzyme electrode comprising:
   an electrically conductive base,
   a selectively permeable membrane having an inner surface and an outer surface and inner surface being mounted to face the electrically conductive base and being prepared from a composition comprising a mixture of (1) an emulsion of resin and (2) a water-soluble polymer material, the emulsion of resin being curable by irradiation with ionizing radiation or ultraviolet ray and containing at least one prepolymer or monomer having ethylenic unsaturation, the selectively permeable membrane being obtained by curing the composition by irradiation with ionizing irradiation or ultraviolet ray, and wherein the selectively permeable membrane is permeable to a substance produced by an enzyme reaction while preventing the permeation of higher molecular weight materials, and
   an immobilized enzyme membrane formed on the outer surface of the selectively permeable membrane, wherein the enzyme is capable of producing the substance which can permeate the selectively permeable membrane which substance must pass through the selectively permeable membrane to contact the electrically conductive base.

2. An enzyme electrode as claimed in claim 1, wherein the thickness of said selectively permeable membrane is 0.1–500 μm.

3. An enzyme electrode as claimed in claim 1, wherein the water-soluble polymer material includes on or more polymer material selected from the group of modified polyvinyl alcohol, gelatine, and gum arabic.

4. An enzyme electrode as claimed in claim 1, wherein the water-soluble polymer material is mixed in a ratio of 0.1–100 parts with 100 parts by weight of the emulsion of resin.

5. An enzyme electrode as claimed in claim 1, wherein the emulsion of resin contains a surface active agent.

6. An enzyme electrode as claimed in claim 1, wherein the selectively permeable membrane is formed by irradiating the composition with an electron beam of an ionizing radiation.

7. An enzyme electrode as claimed in claim 1, wherein the enzyme is an oxidase enzyme capable of producing hydrogen peroxide.

8. An enzyme electrode as claimed in claim 5, wherein the surface active agent is a nonionic surface active agent.

9. An enzyme electrode as claimed in claim 5, wherein the surface active agent is contained in a range of 0.01–20% by weight of the prepolymer or monomer.

10. An enzyme electrode as claimed in claim 6, wherein the quantity of irradiating electron beam is 0.1-10 Mrad.

11. An enzyme electrode comprising:
an electrically conductive base,
a selectively permeable membrane having an inner surface and an outer surface said inner surface being mounted on the electrically conductive base and said membrane being prepared from a composition comprising a mixture of (1) a first emulsion of resin and (2) a water-soluble polymer material, the first emulsion of resin being curable by irradiation with ionizing radiation or ultraviolet ray and containing at least one prepolymer or monomer having ethylenic unsaturation, the selectively permeable membrane being obtained by curing the composition by irradiation with ionizing irradiation or ultraviolet ray, and wherein the selectively permeable membrane is permeable to a substance produced by an enzyme reaction while preventing the permeation of higher molecular weight material, and
an immobilized enzyme membrane formed on the outer surface of the selectively permeable membrane, the immobilized enzyme membrane being obtained by (a) applying on the outer surface of the selectively permeable membrane a composition containing a mixture of (1) a second emulsion of resin which is the same as or different than the above said first emulsion resin and is curable by irradiation of ionizing radiation or ultraviolet ray, and (2) an enzyme which is capable of producing the above said substance which can permeate the selectively permeable membrane, and (b) curing the composition by irradiation with ionizing radiation or ultraviolet ray.

12. An enzyme electrode according to claim 11, wherein the enzyme is mixed into the second emulsion of resin in a range of 0.01-20% by weight on solid of the mixed composition comprising the second emulsion of resin and the enzyme.

13. An enzyme electrode according to claim 11, wherein curing is with an electron beam of ionizing radiation.

14. An enzyme electrode according to claim 11, wherein the enzyme is an oxidase enzyme capable of producing hydrogen peroxide.

15. An enzyme electrode comprising:
an electrically conductive base,
a selectively permeable membrane having an inner surface and an outer surface said inner surface being mounted on the electrically conductive base, said membrane being prepared from a composition comprising a mixture of (1) a first emulsion of resin and (2) a first water-soluble polymer material, the first emulsion of resin being curable by irradiation with ionizing radiation or ultraviolet ray and containing at least one prepolymer or monomer having ethylenic unsaturation, the selectively permeable membrane being obtained by curing the composition by irradiation with ionizing irradiation or ultraviolet ray, and the selectively permeable membrane being permeable to a substance produced by an enzyme reaction while preventing the permeation of higher molecular weight materials, and
an immobilized enzyme membrane formed on the outer surface of the selectively permeable membrane, the immobilized enzyme membrane being obtained by (a) applying on the outer surface of the selectively permeable membrane a composition containing a mixture of
(1) a second emulsion of resin which is the same as or different than the above said first emulsion of resin and which is curable by irradiation of ionizing radiation or ultraviolet ray, (2) a second water-soluble polymer material which is the same as or different than the above said first water-soluble polymer material, and (3) an enzyme which is capable of producing the above said substance which can permeate the selectively permeable membrane, and (b) curing the composition by irradiation with ionizing radiation or ultraviolet ray.

16. An enzyme electrode as claimed in claim 15, wherein the second water-soluble polymer material contains one, or more water-soluble polymers selected from the group of modified polyvinyl alcohol, gelatine, gum arabic, and albumin.

17. An enzyme electrode as claimed in claim 16, wherein the second water-soluble polymer material and the enzyme are added to the emulsion of resin in a range of 0.1-50% by weight on dry basis of the mixed composition.

18. A process of manufacturing an enzyme electrode comprising the steps of:
(a) forming a composition comprising a mixture of (1) an emulsion of resin containing at least one prepolymer or monomer having ethylenic unsaturation curable by irradiation with ionizing radiation or ultraviolet ray and (2) a water-soluble polymer material;
(b) irradiating the composition with ionizing radiation or ultraviolet ray to cure the composition and thereby form a selectively permeable membrane having an inner surface and an outer surface and which is permeable to a substance produced by an enzyme reaction while preventing the permeation of higher molecular weight substances;
(c) forming an immobilized enzyme membrane on the outer surface of the selectively permeable membrane; and
(d) mounting the selectively permeable membrane having the immobilized enzyme membrane formed thereon with an electrically conductive base so that the inner surface of the selectively permeable membrane faces the said base.

19. A process of manufacturing an enzyme electrode comprising the steps of:
(a) forming a composition comprising a mixture of (1) an emulsion of resin containing at least one prepolymer or monomer having ethylenic unsaturation curable by irradiation with ionizing radiation or ultraviolet ray and (2) a water-soluble polymer material, on an electrically conductive base;
(b) irradiating the composition with ionizing radiation or ultraviolet ray to cure the composition and thereby form a selectively permeable membrane having an inner surface and an outer surface and which is permeable to a substance produced by an enzyme reaction while preventing the permeation of higher molecular weight substances the said inner surface being adjacent to said electrically conductive base; and
(c) forming an immobilized enzyme membrane on the outer surface of the selectively permeable membrane.

* * * * *